(12) United States Patent
Gustafson et al.

(10) Patent No.: US 9,248,213 B2
(45) Date of Patent: Feb. 2, 2016

(54) ABSORBENT ARTICLE

(75) Inventors: Ingrid Gustafson, Åsa (SE); Ulrika Husmark, Mölnlycke (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 1200 days.

(21) Appl. No.: 12/158,107

(22) PCT Filed: Dec. 22, 2005

(86) PCT No.: PCT/SE2005/002029
§ 371 (c)(1),
(2), (4) Date: Jun. 19, 2008

(87) PCT Pub. No.: WO2007/073265
PCT Pub. Date: Jun. 28, 2007

(65) Prior Publication Data
US 2008/0294133 A1 Nov. 27, 2008

(51) Int. Cl.
*A61F 13/15* (2006.01)
*A61F 13/20* (2006.01)
*A61L 15/36* (2006.01)
*A61F 13/472* (2006.01)
*A61F 13/505* (2006.01)
*A61F 13/84* (2006.01)

(52) U.S. Cl.
CPC ........... *A61L 15/36* (2013.01); *A61F 13/47218* (2013.01); *A61F 13/505* (2013.01); *A61F 13/8405* (2013.01); *A61F 2013/15097* (2013.01); *A61F 2013/8408* (2013.01)

(58) Field of Classification Search
CPC .............. A61F 13/505; A61F 13/8405; A61F 2013/8408; A61L 15/36
USPC .............................. 604/358–361, 367, 385.01
See application file for complete search history.

(56) References Cited

U.S. PATENT DOCUMENTS 3,490,454 A 1/1970 Godfarb et al.
3,783,869 A 1/1974 Schnipper
(Continued)

FOREIGN PATENT DOCUMENTS

EP 1 035 818 9/2000
EP 1 118 342 A1 7/2001
(Continued)

OTHER PUBLICATIONS

Form PCT/ISA/210 (International Search Report) dated Jul. 13, 2006.
(Continued)

*Primary Examiner* — Michele M Kidwell
(74) *Attorney, Agent, or Firm* — Buchanan Ingersoll & Rooney PC (57) ABSTRACT

An absorbent article such as a sanitary napkin, panty liner, tampon, diaper, pant diaper, adult incontinence guard, containing a bacterial composition (8) in a lipid phase (9), the bacterial composition containing at least one lactic acid producing bacterial strain. The lipid phase (9) containing said bacterial composition (8) is applied on or in a carrier member (10) which at least before use of the article is impermeable to the lipid phase. The carrier member is located on a wearer facing side of the absorbent structure (4) so as to prevent significant transfer of the lipid phase into the absorbent structure.

26 Claims, 5 Drawing Sheets

(56) References Cited

U.S. PATENT DOCUMENTS

| | | | |
|---|---|---|---|
| 4,015,604 A * | 4/1977 | Csillag | 604/382 |
| 4,518,696 A | 5/1985 | Gerhrman et al. | |
| 7,919,666 B2 * | 4/2011 | Odorzynski | 604/359 |
| 2001/0033838 A1 * | 10/2001 | Farmer | 424/115 |
| 2004/0172001 A1 | 9/2004 | Tengberg et al. | |
| 2004/0243076 A1 * | 12/2004 | Husmark et al. | 604/358 |

FOREIGN PATENT DOCUMENTS

| | | |
|---|---|---|
| JP | 11-504048 T | 4/1999 |
| JP | 2001-245660 | 9/2001 |
| JP | 2001-340379 | 12/2001 |
| JP | 2003-502225 T | 1/2003 |
| JP | 2003-520105 T | 7/2003 |
| JP | 2003-529681 T | 10/2003 |
| WO | WO 84/04675 | 12/1984 |
| WO | WO 92/13577 A1 | 8/1992 |
| WO | WO 97/02846 A1 | 1/1997 |
| WO | WO 97/29762 | 8/1997 |
| WO | WO 98/46261 A1 | 10/1998 |
| WO | WO 99/17813 A1 | 4/1999 |
| WO | WO 99/27876 A1 | 6/1999 |
| WO | WO 99/45099 A1 | 9/1999 |
| WO | WO 00/35502 A1 | 6/2000 |
| WO | WO 00/63487 | 10/2000 |
| WO | WO 00/76878 | 12/2000 |
| WO | WO 01/13956 A2 | 3/2001 |
| WO | WO 01/52912 | 7/2001 |
| WO | WO 02/28446 A1 | 4/2002 |
| WO | WO 03/053397 A1 | 7/2003 |
| WO | WO 2004/101008 | 11/2004 |
| WO | WO 2004/105822 | 12/2004 |

OTHER PUBLICATIONS

Form PCT/ISA/237 (Written Opinion of the International Searching Authority) dated Jul. 13, 2006.

G. B. Hill et al., "Bacteriology of the Vagina", Scand. J. Urol Nephrol., 1984, vol. 86, pp. 23-29 (cited on p. 1 of the specification).

Arkadéva et al., "Preservation of Lactic Acid Bacteria", Biologicheskie Nauki, 1983, vol. 2, pp. 101-104, with English language Abstract (cited on p. 3 of the specification).

Stoianova et al., "Comparison of Methods of Storing Lactic Acid Bacteria", Mikrobiologiia, 2000, vol. 69, pp. 98-104, with English language Abstract (cited on p. 3 of the specification).

Supplementary European Search Report issued in the corresponding Application No. 05823733.0-2123 dated Apr. 21, 2010.

An English Translation of the Office Action (Notice of Reasons for Rejection) dated Jan. 4, 2011, issued in the corresponding Japanese Patent Application No. 2008-547151.

\* cited by examiner

ABSORBENT ARTICLE

FIELD OF INVENTION

The present disclosure refers to an absorbent article such as a sanitary napkin, panty liner, tampon, diaper, pant diaper, adult incontinence guard. More specifically it refers to such articles containing bacterial composition comprising at least one lactic acid producing bacterial strain

TECHNICAL BACKGROUND

The urogenital area harbors a complex microbial ecosystem comprising more than 50 different bacterial species (Hill et al., Scand. J. Urol. Nephrol. 1984; 86 (suppl.) 23-29). The dominating species for fertile women in this area are lactic acid producing bacteria belonging to the genus *Lactobacillus*. These lactic acid producing members are important for retaining a healthy microbial flora in these areas, and act as probiotic bacteria with an antagonistic effect against pathogenic microbial species. Lactic acid producing bacteria inhibit growth and colonization by other microorganisms by occupying suitable niches for colonization, by forming biofilms and competing for available nutrients, thereby excluding colonization by harmful microorganisms. Also, the production of hydrogen peroxide, specific inhibiting substances, such as bacteriocines, and organic acids (including lactic acid and acetic acid) that lower the pH, inhibit colonization by other microorganisms.

The microbial ecosystem of a healthy individual can be disturbed by the use of antibiotics, during hormonal changes, such as during pregnancy or use of contraceptives with estrogen, during menstruation, after menopause, in people suffering from diabetes etc. Also, microorganisms may spread from the anus to the urogenital area, thereby causing infections. This results in a disturbance of the normal microbial flora and leaves the individual susceptible to microbial infections that cause vaginitis, urinary tract infections and ordinary skin infections. Microorganisms commonly associated with these kinds of infections belong to the genera *Escherichia, Enterococcus, Psedomonas, Proteus, Klebsiella, Streptococcus, Staphylococcus, Gardnerella* and *Candida*. Women are at particular risk due to their shorter distance between the anus and the urogenital tract; specially at risk are young women, who not yet have a well developed microflora in the urogenital area and older women, who no longer have a protective flora.

One way to reduce the problems with the kinds of infections described above is to have a good personal hygiene. However, excessive use of cleaning agents not only decrease the amount of harmful microbes, but can harm the beneficial microbial flora, again render it susceptible for pathogenic species to colonize and cause infections. Alternatively, administration of lactic acid producing bacteria to the urogenital area and the skin in order to outcompete pathogenic species and facilitate reestablishment and maintenance of a beneficial microbial flora in these areas, have been found to be a successful means to treat and prevent microbial infections.

It has been suggested that lactic acid producing bacteria can be delivered via absorbent products, such as diapers, sanitary napkin, incontinence guards, panty liners and tampons, as described in, for example, WO 92/13577, WO 97/02846, WO 99/17813, WO 99/45099 and WO 00/35502.

A major problem with providing products intended to be used for transfer of lactic acid producing bacteria, is that the bacteria have to retain viability during transport and storage of the products. A major problem with products comprising lactic acid producing bacteria is that the bacteria rapidly lose viability under semi-moist conditions, and it is therefore important that the products are not exposed to moisture.

With "semi-moist" conditions is meant that the water activity ($a_w$) is between about 0.2 and about 0.9. Water activity $a_w$ measures the vapour pressure generated by the moisture present in a hygroscopic product.

$$a_w = p/p_s,$$

where:
p: partial pressure of water vapour at the surface of the product
$p_s$: saturation pressure, or the partial pressure of water vapour above pure water at the product temperature Water activity reflects the active part of moisture content or the part which, under normal circumstances, can be exchanged between the product and its environment.

Water activity is usually defined under static conditions of equilibrium. Under such conditions, the partial pressure of water vapour (p) at the surface of the product is equal to the partial pressure of water vapour in the immediate environment of the product. Any exchange of moisture between the product and its environment is driven by a difference between these two partial pressures.

One way to partly overcome this problem has been to supply products with freeze-dried lactic acid producing bacteria. However, if the bacteria in the products are not protected from moisture after manufacturing of the products, the air humidity will subsequently kill the bacteria and the shelf-life of such products will then be shortened. Another disadvantage with the direct application of dried lactic acid producing bacteria to a hygiene product, such as an absorbent product, is that transfer of the bacteria to the urogenital area will be low.

In order to overcome the problem with air humidity decreasing the shelf-life of products containing lactic acid producing bacteria it has been suggested to prepare dispersions of lactic acid producing bacteria and a hydrophobic substance, such as a fat or an oil. Research experiments have shown that storage in sterile vaseline oil results in a high level of viable lactobacilli cells after 8 months of storage (Arkadéva et al., N A. Nauchnye Doklady Vysshei Shkoly. Biologicheskie Nauki, 1983, 2:101-104). However, Stoianova et al. (Mikrobiologiia, 2000, 69:98-104), found that immersion in mineral oil was not effective to preserve viability of lactic acid producing bacteria. U.S. Pat. No. 4,518,696 describes liquid suspensions of Lactobacilli in sunflower oil for oral administration to animals. However, none of the above references are concerned with the problems associated with retaining a high viability of lactic acid producing bacteria on hygiene products to be used to administer lactic acid producing bacteria to the urogenital area of a subject.

There are additional examples of the combination lactic acid producing bacteria and an oil, although these do not describe the effect of the oil on the survival of the lactic acid producing bacteria. WO 01/13956 describes the use of pharmaceutical compositions comprising Emu oil, antimicrobial agents and/or *Bacillus coagulans* to be used for antimicrobial treatments. However, *Bacillus coagulans* is not naturally occurring in the normal human urogenital flora and is mainly used as odor inhibitor and is not adapted to improve the microbial flora in humans. *Bacillus coagulans* is forming spores and is therefore not sensitive for normal moisture. WO 02/28446 describes the use of an essentially hydrophobic carrier and freeze-dried lactic acid producing bacteria to prepare a distribution to be applied to an absorbent product. The hydrophobic carrier was mainly chosen to overcome problems with applying the bacteria to the absorbent product during manufacturing, but the carrier also protects the bacteria from air humidity.

In conclusion, there is still a need to develop products for delivery of lactic acid producing bacteria to the urogenital area that are convenient to use, result in efficient transfer of the bacteria to the area where they are applied and that can be stored for long time periods without loss of viability of the bacterial cells.

OBJECT AND SUMMARY

The above defined problems are solved by an absorbent article containing a bacterial composition in a lipid phase, said bacterial composition containing at least one lactic acid producing bacterial strain, said article comprising an absorbent structure, wherein the lipid phase containing said bacterial composition is applied on a carrier member which at least before use of the article is impermeable to said lipid phase, said carrier member being located on a wearer facing side of the absorbent structure so as to prevent significant transfer of the lipid phase into the absorbent structure.

In one aspect said carrier member at least partly encloses the lipid phase with the bacterial composition contained therein.

In a further aspect the carrier member comprises a sheet having at least one pocket or well formed therein containing the lipid phase and bacterial composition.

It is desirable that said pocket or well has a depth of at least 2 mm, preferably at least 4 mm and more preferably at least 5 mm. It is further preferred that the pocket or well has a depth of no more than 10 mm, preferably no more than 8 mm.

According to one embodiment the carrier member is provided with at least two pockets or wells containing the lipid phase and bacterial composition. In a further embodiment the pockets or wells are located spaced apart a distance (b) of at least 5 mm. Preferably the pockets or wells are spaced apart in the longitudinal direction of the article.

In one aspect the least one pocket or well is covered by a cover material that is impermeable to the lipid phase. The cover material may be of the same or of a different material as the carrier member and is upon use of the article removable by melting, dissolving, peeling off and/or rupturing.

In a further aspect the lipid phase with the bacterial composition is completely enclosed by the carrier member, which is in the form of a bubble, tube or pouch. According to one embodiment at least part of said bubble, tube or pouch has a minimum cross dimension of at least 2 mm, preferably at least 4 mm and more preferably at least 5 mm.

The article may comprise at least two of said bubbles, tubes or pouches each containing the lipid phase and bacterial composition. In one aspect said bubbles, tubes or pouches are located spaced apart a distance (b) of at least 5 mm. Preferably they are spaced apart in the longitudinal direction of the article.

In one aspect the lipid phase is a wax and/or an oil. The wax may be chosen from a plant wax, a mineral wax, an animal wax, a silicon wax and mixtures thereof. In one embodiment the wax is a mineral wax which preferably as a main component contains petrolatum.

In a further aspect the carrier member is chosen from polymer films, metal foils and laminates there from. The polymer film may water soluble. The carrier member may be chosen from the following materials: polyethylene, polypropylene, polyamide, polyesters, polyurethanes, polyvinyl alcohols, polyvinylacetate, polyethers, ionomers and copolymers thereof, aluminium foil, laminates of polymer films and aluminium foil.

The carrier member may be water vapour impermeable. An example of such a material is aluminium foil having a thickness of at least 9 μm. A suitable water vapour impermeable carrier material is a laminate of a polymer film and aluminium foil, said aluminium foil having a thickness of at least 9 μm.

In one embodiment the at least one carrier member holding the lipid phase and bacterial composition is applied on the wearer facing side of the article or below one or more layers of the article permitting penetration of the lactic acid producing bacterial strain to the wearer.

BRIEF DESCRIPTION OF THE DRAWINGS

FIG. 4 a-e illustrates carrier members according to the invention having different shapes.

FIG. 6 a-c shows a third embodiment of an absorbent article during different stages of opening the carrier member for exposing the lipid phase and bacterial composition.

FIG. 7 a-c shows a fourth embodiment of an absorbent article during different stages of opening the carrier members.

DETAILED DESCRIPTION OF THE PREFERRED EMBODIMENTS

The term "absorbent article" refers to products that are placed against the skin of the wearer to absorb and contain body exudates, like urine, faeces and menstrual fluid. The disclosure mainly refers to disposable absorbent articles, which means articles that are not intended to be laundered or otherwise restored or reused as an absorbent article after use. Examples of disposable absorbent articles include feminine hygiene products such as sanitary napkins, panty liners, tampons and sanitary panties; diapers and pant diapers for infants and incontinent adults; incontinence pads.

By "probiotic composition" or "bacterial composition" is meant a composition comprising probiotic bacteria, i.e. bacteria that have the ability to reestablish the natural microbial flora of the host. The probiotic preparation according to embodiments of the present invention further comprises a lipid phase.

By "dispersion" is meant a mixture of at least two phases which are insoluble or have a limited solubility in one another and wherein one phase forms solid particles, liquid droplets or gas bubbles in the other phase.

Preferred "lactic acid producing bacteria" include bacteria from the genera *Lactobacillus, Lactococcus* and *Pediococcus*. Preferably the selected bacterium used is from the species *Lactococcus lactis, Lactobacillus acidophilus, Lactobacillus curvatus, Lactobacillus plantarum* or *Lactobacillus rhamnosus*. More preferably the bacterial strain is selected from *Lactobacillus plantarum*. Even more preferably the lactic acid producing bacterium is *Lactobacillus plantarum* 931 (deposition No. (DSMZ): 11918). The bacteria are preferably isolated from the natural flora of a healthy person, preferably the bacteria are isolated from the skin or urogenital area or orally.

By "lipid phase" is meant a water-insoluble organic phase with a fatty character. Lipids suitable to be used in the lipid phase include petroleum-derived lipids, synthetic lipids, and animal- and plant-derived lipids. Preferred lipids are waxes and oils and mixtures thereof.

Examples of "additional components" include, but are not limited to, agents protecting the bacterial cells during drying of the bacteria, agents acting as nutrient for bacterial propagation, and skin caring agents. Further examples of suitable additional components are given below.

Figure 1:
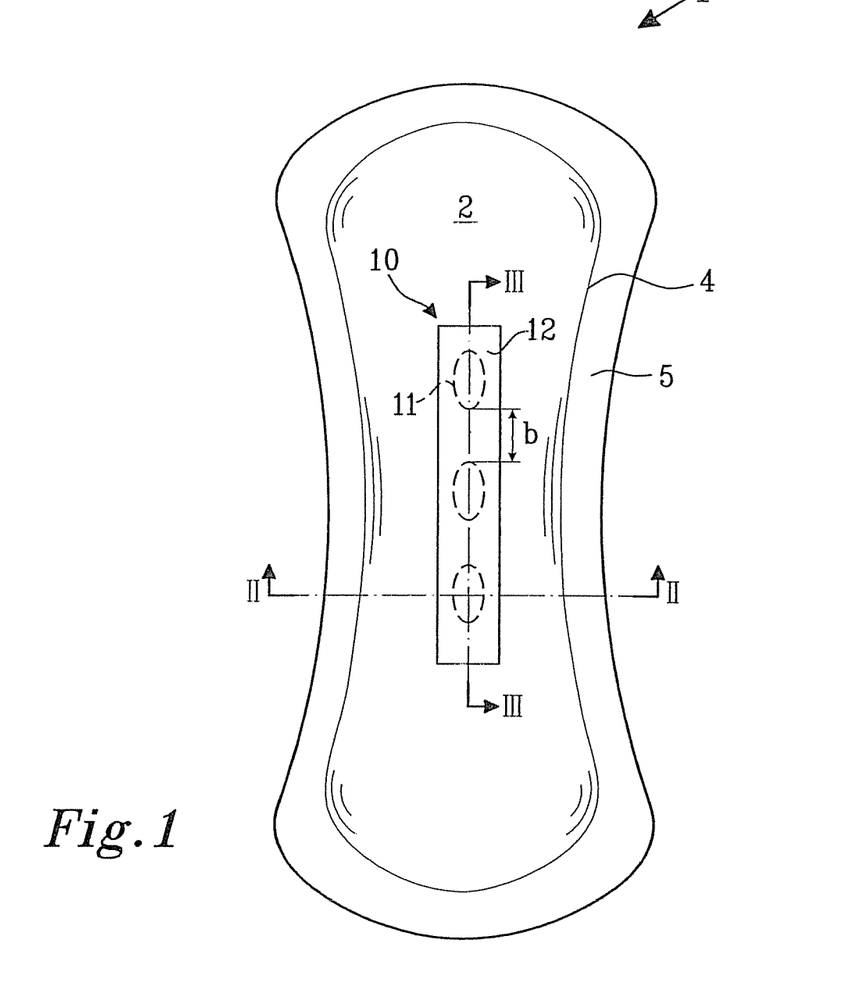
FIG. 1 is a plan view of an embodiment of an absorbent product according to the present invention.
Figure 2:
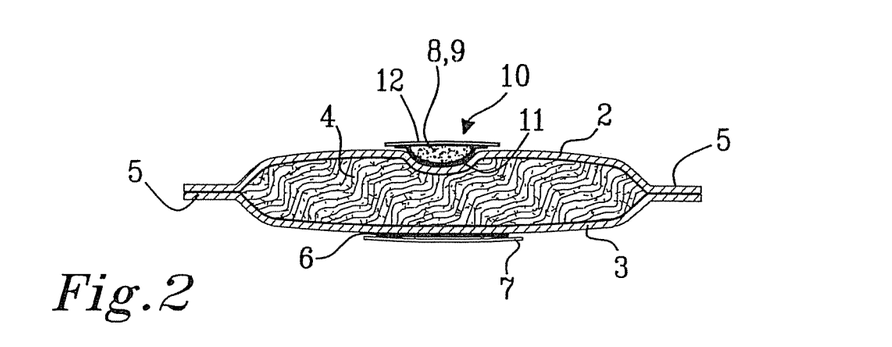
FIG. 2 is a cross sectional view through the absorbent article according to the line II-II in FIG. 1.

FIGS. 1 and 2 show an embodiment of a sanitary napkin 1 which typically comprises a liquid permeable topsheet 2, a liquid impermeable backsheet 3 and an absorbent structure 4 enclosed there between. The liquid permeable topsheet 2 can be composed of a nonwoven material, e g spunbonded, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The topsheet material may further be composed of tow fibres, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and be readily penetrated by body fluid, such as urine or menstrual fluid.

The liquid impermeable backsheet 3 may consist of a thin plastic film, e.g. a polyethylene or polypropylene film, a nonwoven material coated with a liquid impervious material, a hydrophobic nonwoven material, which resists liquid penetration or laminates of plastic films and nonwoven materials. The backsheet material may be breathable so as to allow vapour to escape from the absorbent structure, while still preventing liquids from passing through the backsheet material.

The topsheet 2 and the backsheet material 3 have a somewhat greater extension in the plane than the absorbent structure 4 and extend outside the edges thereof. The layers 2 and 3 are connected to each other within the projecting portions 5 thereof, e.g. by gluing or welding by heat or ultrasonic. The topsheet and/or the backsheet may further be attached to the absorbent structure by any method known in the art, such as adhesive or welding by heat or ultrasonic etc. The absorbent structure may also be unattached to the topsheet and/or the backsheet.

A fastening means in the form of a region 6 of an adhesive is provided on the side of the backsheet facing away from the wearer in use. The adhesive may releasably attach to the undergarment of the wearer. A release paper 7 protects the adhesive region before use. The adhesive region 6 may have any suitable configuration, such as elongate or transverse strips, dots, full-coated areas etc.

In other embodiments of absorbent articles other types of fasteners, like friction fasteners, tape tabs or mechanical fasteners like hook-and-loop fasteners etc may be used to fasten the articles to the underwear or around the waist of the wearer. Some absorbent articles are in the form of pants and therefore do not need special fastening means. In other cases the absorbent article is worn in special elastic pants without the need for additional fasteners.

The absorbent structure 4 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent structure. It is also common to have absorbent structures comprising layers of different material with different properties with respect to liquid acquisition capacity, liquid distribution capacity and storage capacity. This is well-known to the person skilled in the art and does therefore not have to be described in detail. The thin absorbent bodies, which are common in today's absorbent articles, often comprise a compressed mixed or layered structure of cellulosic fluff pulp and superabsorbent. The size and absorbent capacity of the absorbent structure may be varied to be suited for different uses such as sanitary napkins, pantiliners, adult incontinence pads and diapers, baby diapers, pant diapers, etc.

It is understood that the absorbent article described above and shown in the drawings only represents one non-limiting example and that the present invention is not limited thereto, but can be used in any type of absorbent articles as defined above.

The object is to provide hygiene products, such as sanitary napkins, tampons, panty-liners, diapers, incontinence guards, hygiene tissues etc. suitable for absorbing bodily fluids and simultaneously delivering probiotic lactic acid producing bacteria to the skin, or more preferably, the urogenital area. Embodiments of the present invention seek to solve the problems associated with providing products comprising lactic acid producing bacteria, such as problems with bacterial survival, transfer to skin and costs and effectiveness of manufacturing.

The absorbent article contains a probiotic preparation comprising a dried bacterial composition 8 which is mixed with a lipid phase 9. The hydrophobic character of the lipid phase decreases the amount of air humidity which reaches the bacterial cells dispersed in the lipid phase, thereby increasing the survival time for the bacteria in the bacterial composition. Dispersing the lactic acid producing bacteria in a lipid phase has the additional advantage that transfer of the bacteria to the skin and/or urogenital area is enhanced compared to when no lipid phase is used. When the product is used, the lipid phase softens when exposed to body heat and the bacterial composition is transferred to the skin. When the bacteria come in contact with moisture after delivery to the skin, they are reactivated, start to grow and perform their probiotic action.

Further additives like contact sorption drying carriers, as disclosed in US 2004/0243076, may be present in the bacterial composition. With "contact sorption carriers" are meant substances that have the ability to take up moisture from the ambient environment. Examples of contact sorption drying carriers are, but not limited to, oligo- and polysaccharides and inorganic agents.

Other additives may also be present in the bacterial composition. Examples of such additives include, but are not limited to, agents protecting the bacterial cells during drying of the bacteria, such as sugars (e.g. maltose, glucose, sucrose, trehalose, fructose), proteins (e.g. skim milk, albumin), amino acids (e.g. sodium glutamate), polyols (e.g. xylitol), mannitol and sorbitol, pH-regulating agents (e.g. lactic acid) and antioxidants (e.g. sodium ascorbate). Additional components also include nutrients that enhance bacterial propagation once the bacteria are activated by moisture after they are delivered to the skin or urogenital area. Additional components can also form part of the probiotic preparation. Suitable additional components also include skin caring substances e.g. lipid soluble skin caring substances, such as vitamin A and E, skin caring oils, such as chamomile oils (Bisabolol), eucalyptus oil, lavender oil and phytosterols. Additional components may also include a preservation matrix according to WO 98/46261.

The lipid phase 9 is a wax and/or an oil. The wax is preferably chosen from plant waxes, mineral waxes, silicone waxes, animal waxes and mixtures thereof. Preferred mineral waxes are paraffin waxes, micro waxes, petrolatum and mixtures thereof. One example of a preferred wax is petrolatum. The lipid phase can also be a mixture of wax and oil. Important characteristics of the lipid phase are that it should be possible to disperse the bacterial composition in the lipid phase at a temperature of between 20 and 50° C., preferably between 20 and 25° C. and that the water content is low, below 4 weight %, preferably below 2 weight %. The melting behaviour of the lipid phase is a further important factor, which will be discussed in further detail below.

The probiotic preparation comprising the lipid phase containing the bacterial composition is applied on or is at least partially encased by a carrier member 10 which is located on a wearer facing side of the absorbent structure 4. The carrier member 10 is either located on top of, i.e. on the wearer facing side of the topsheet 2, or between the topsheet and the absorbent structure 4. The carrier member 10 is of a material that is impermeable to the lipid phase, so that any significant transfer of the lipid phase into the absorbent structure 4 is prevented.

Suitable materials for the carrier member 10 are polymer films, metal foils and laminates there from. The polymer film may be water soluble or water insoluble, but preferably water soluble. Examples of suitable polymers for the carrier member are: polyethylene, polypropylene, polyamide, polyesters, polyurethanes, polyvinyl alcohols, polyvinylacetate, polyethers, ionomers and copolymers thereof, An example of a suitable metal foil is aluminium foil. Laminates of polymer films and metal foils may also be used as carrier member material. The carrier member may be water vapour impermeable. An example of a water vapour impermeable material is an aluminium foil having a thickness of at least 9 μm, and a suitable water vapour impermeable carrier member material is a laminate of a polymer film and aluminium foil, wherein the aluminium foil has a thickness as defined above.

Figure 3:
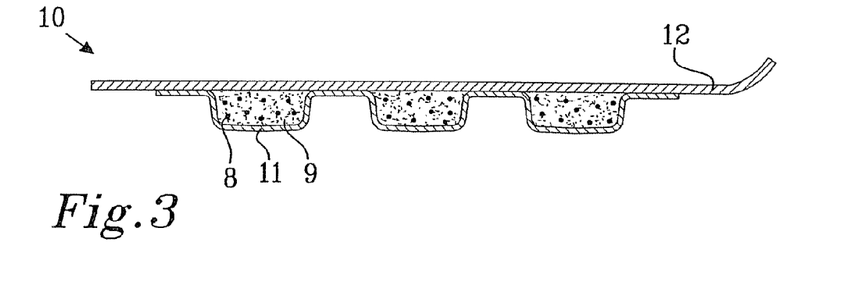
FIG. 3 is a cross sectional view according to the line III-III in FIG. 1.

The carrier member 10 preferably at least partly encloses the probiotic preparation comprising the lipid phase containing the bacterial composition. This may according to one embodiment illustrated in FIGS. 1-3 be accomplished by having one ore more pockets or wells 11 formed in a substantially flat carrier member 10. The probiotic preparation is applied in these pockets or wells 11. It is preferred that these pockets or wells 11 have a depth, a, of at least 2 mm, preferably at least 4 mm and more preferably at least 5 mm.

It has been shown that after 3-6 months the bacterial survival of Lactobacillus dispersed in petrolatum in aluminium wells of a depth of 1 mm was significantly lower than for those dispersed in petrolatum in aluminium wells having a depth of 3 and 5 mm. In all cases the diameter of the wells were 17 mm. This test is illustrated in Table 1 below.

It is further preferred that the pockets or wells 11 have a depth of no more than 10 mm, preferably no more than 8 mm.

According to one embodiment the carrier member 10 is provided with at least two pockets or wells 11 containing the probiotic preparation. Preferably the pockets or wells are located spaced apart a distance, b, of at least 5 mm, preferably at least 10 mm, in the longitudinal direction of the article.

The pockets or wells 11 are before use of the article covered by a material 12 that is impermeable to the lipid phase. This cover material may be the same as the carrier member material or a different material. It may be water soluble so that it is readily dissolved when contacted with body fluid. It may alternatively be water insoluble, at which it must be removed or ruptured before using the article. This may be accomplished in many different ways, for example by a pull string having a free end and which extends below the cover material, by peeling of the cover material, by squeezing and rupturing the cover material etc. The cover material 12 may further be of a material that melts when exerted to body temperature and thus exposes the probiotic preparation.

The carrier member 10 may also be in the form of a bubble, pouch or tube that encloses the probiotic preparation. The article may comprise two or more of said bubbles, pouches or tubes each containing the probiotic preparation. In the case of two or more bubbles, pouches or tubes, these are preferably located spaced apart a distance, b, of at least 10 mm in the longitudinal direction of the article.

Figure 4A:
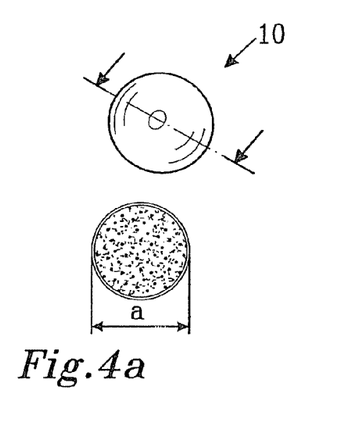
Figure 4B:
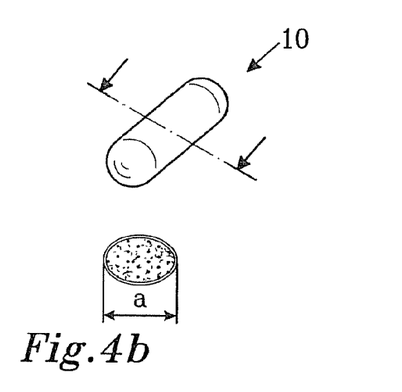
Figure 4C:
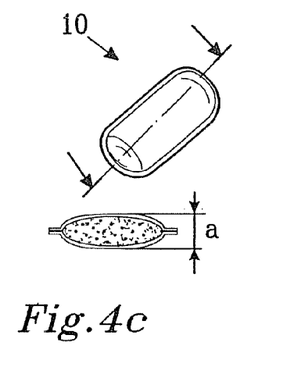
Figure 4D:
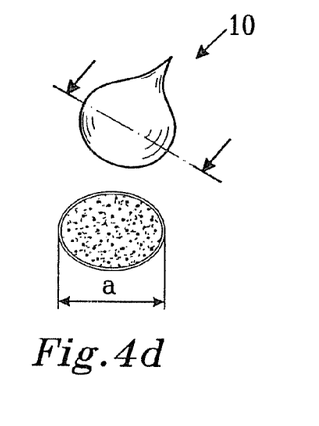
Figure 4E:
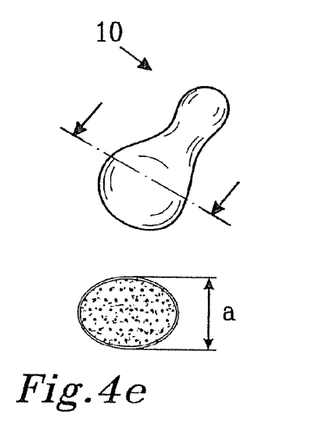

It is preferred that each carrier member bubble, pouch or tube 10 has a minimum cross dimension of at least 2 mm, preferably at least 4 mm and more preferably at least 5 mm, in order to ensure a good bacterial survival in the probiotic preparation. The "minimum cross dimension" is herein defined as the cross dimension in the direction in which the capsule has its minimum cross dimension, i.e. is thinnest. This is illustrated in FIG. 4 *a-e*, wherein FIG. 4*a* shows a spherical bubble and FIG. 4*b* a cylindrical tube, both of which having a substantially circular cross section. In this case the minimum cross dimension, a, is simply the diameter of the bubble or tube. FIG. 4*c* show a "flat" pouch, wherein the minimum cross dimension, a, is the thickness of the pouch. FIG. 4*d* illustrates a drop-shaped bubble, having a thicker substantially spherical portion with a diameter corresponding to the "minimum cross dimension", a. FIG. 4*e* illustrates a tube or pouch having a varying cross dimension over its length, wherein at least one portion of the tube or pouch has a minimum cross dimension or thickness, a, as claimed. Thus there may be other portions of the tube or pouch having smaller cross dimensions than the claimed "minimum cross dimension".

The carrier member 10 is placed in an absorbent article either on the wearer facing side of the topsheet material 2, immediately below the topsheet or close enough below the topsheet to allow the bacterial composition to penetrate through the topsheet to the user of the article. It is important that it is placed on the wearer facing side of the absorbent

TABLE 1

| Depth of wells (mm) | Amount petrolatum (mg) | Amount of Lb 0-value (Cfu/g) | 1 month | 2 mon. | 3 mon. | 4 mon. | 5 mon. | 6 mon. |
|---|---|---|---|---|---|---|---|---|
| 1 | 200 | 1.5E8 | 7.5E7 | 1.5E7 | 2.9E6 | 4.2E5 | 1.7E4 | 6.6E3 |
| 3 | 600 | 1.5E8 | 6.3E7 | 3.0E7 | 4.4E7 | 2.0E7 | 2.0E7 | 1.8E7 |
| 5 | 1000 | 1.5E8 | 8.0E7 | 5.0E7 | 5.8E7 | 4.6E7 | 2.1E7 | 3.4E7 | structure 4 so that leakage of the probiotic preparation to the absorbent structure 4 is prevented at least before use of the article.

Figure 5:
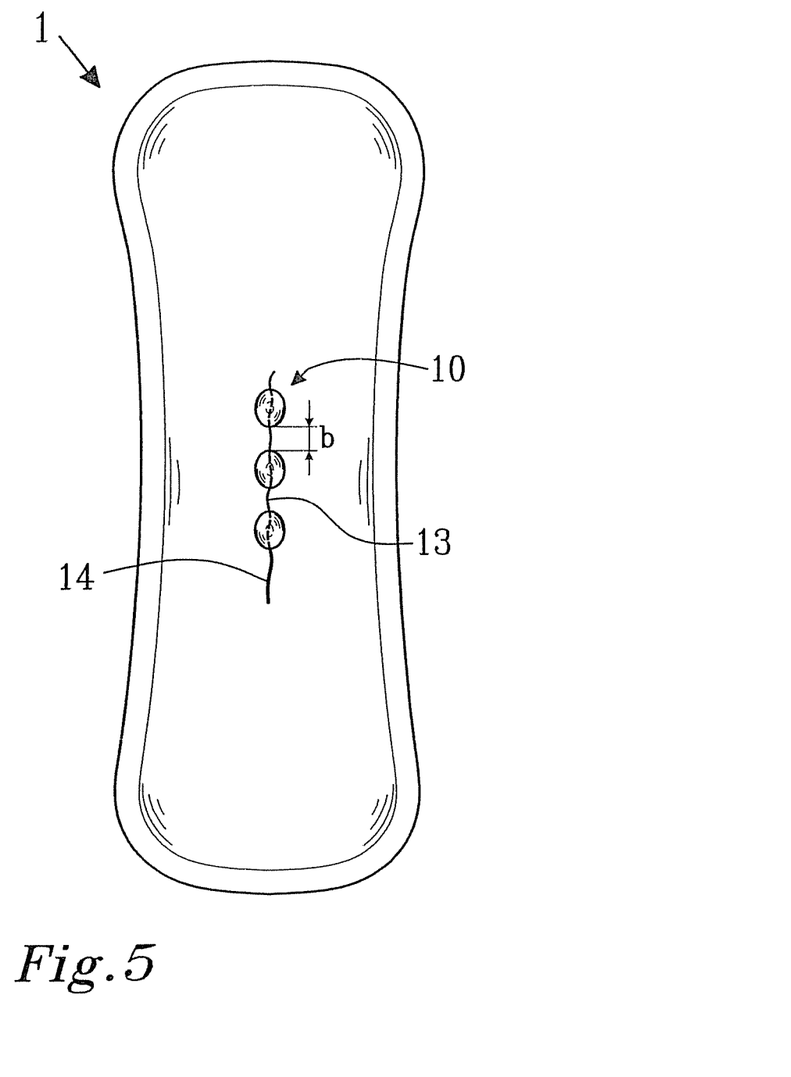
FIG. 5 shows a further embodiment of an absorbent article according to the invention.

FIG. 5 illustrates an absorbent article in the form of a sanitary napkin, pantiliner, incontinence guard or the like, provided with two carrier members 10 in the form of bubbles, which are spaced apart a distance, b, in the longitudinal direction of the article.

The bubbles 10 are located and attached to, for example by an adhesive, to the wearer facing side of the topsheet 2. A string 13 is embedded in the bubbles 10 and has a free end 14 protruding outside the bubbles. By pulling the string 13 the bubbles 10 are ruptured and the probiotic preparation held therein is released.

Figure 6A:
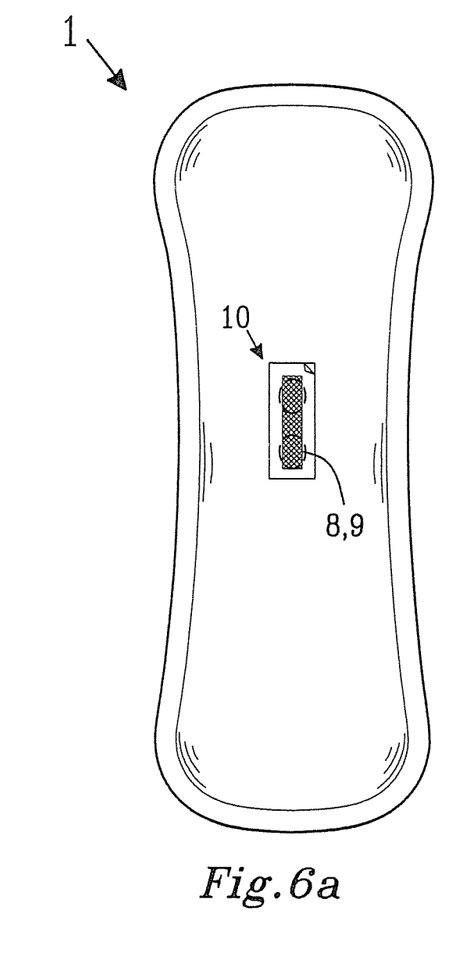
Figure 6B:
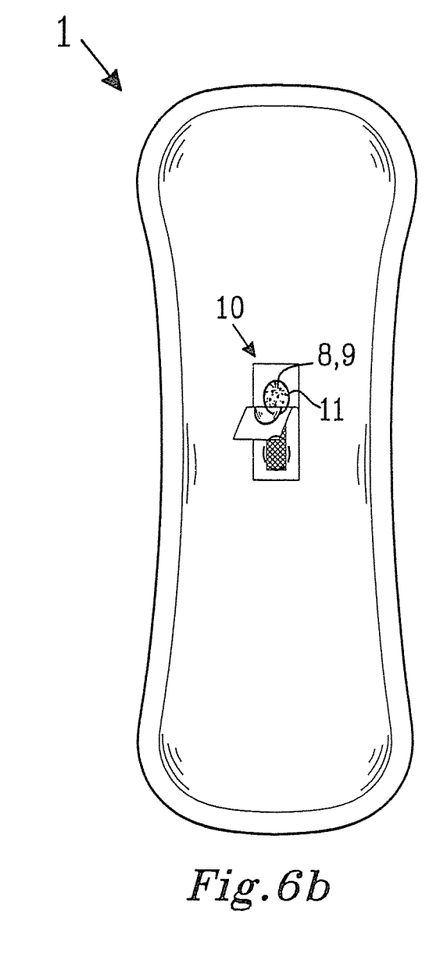
Figure 6C:
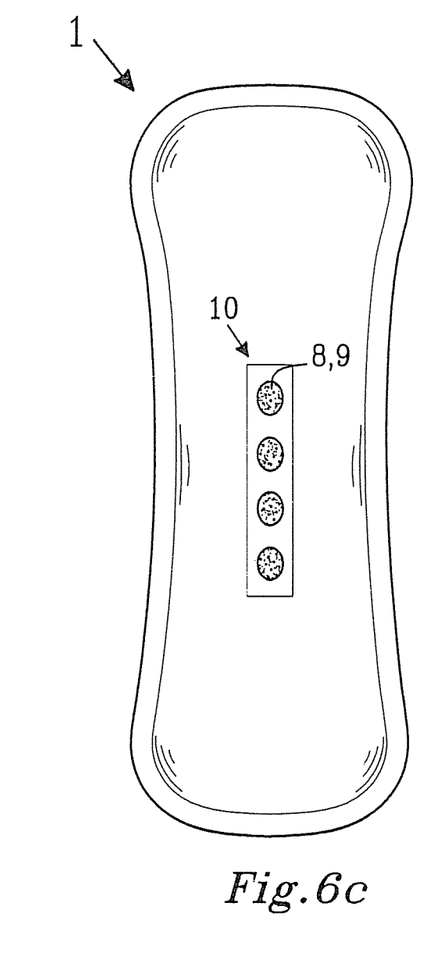

FIG. 6 a-c illustrate a further embodiment of an absorbent article having a carrier member 10 in the form of a pouch, which is adhered to the wearer facing side of the topsheet 2. The upper layer of the pouch is peeled open upon use of the article and folded over the surface of the article, as illustrated in FIGS. 6 b and c, at which the probiotic preparation is exposed.

Figure 7A:
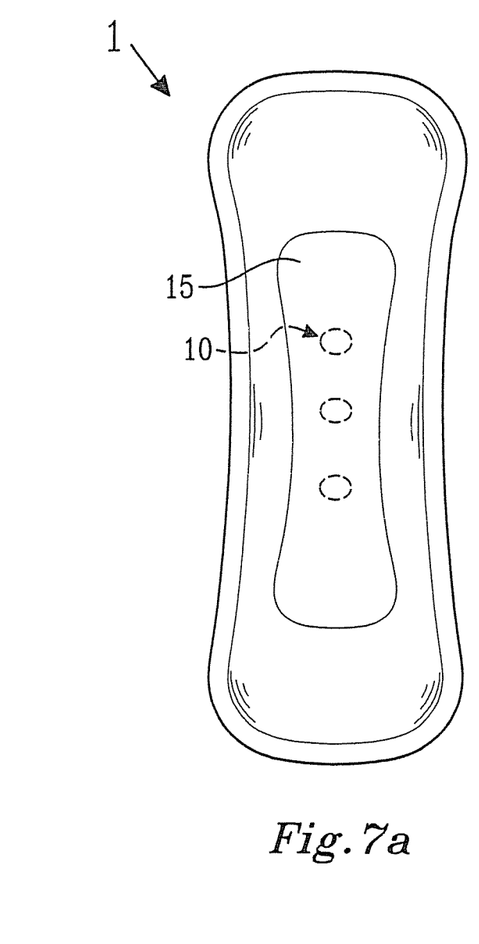
Figure 7B:
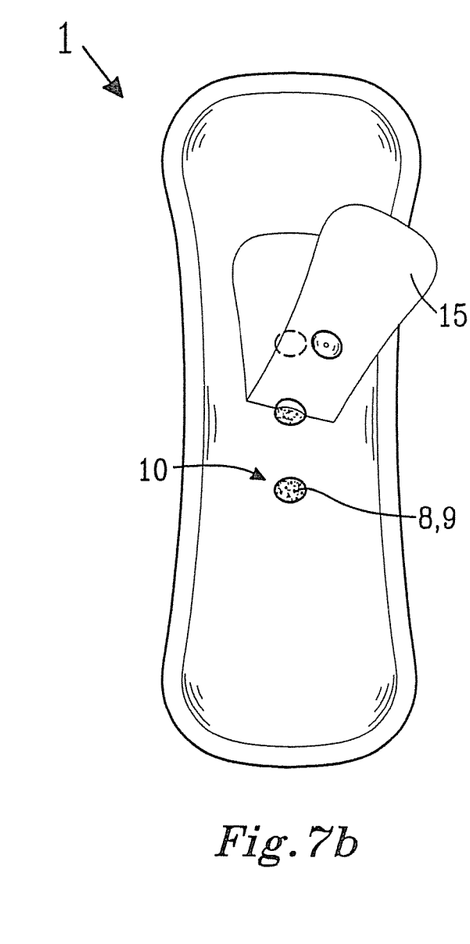
Figure 7C:
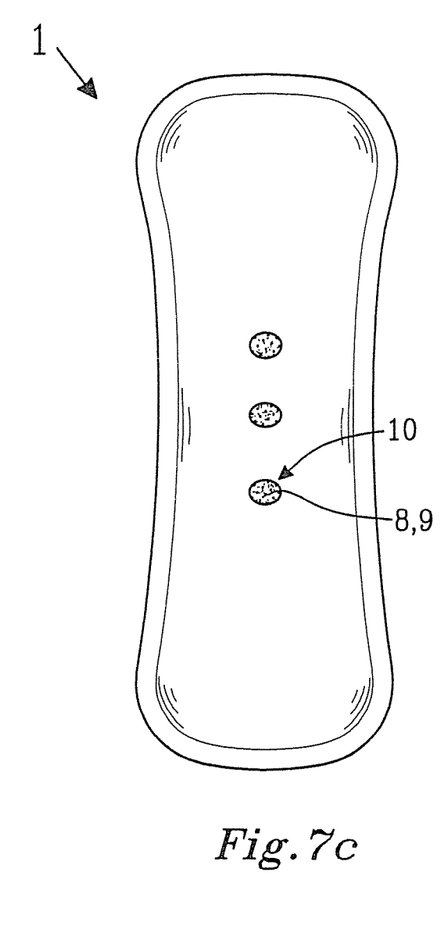

According to a still further embodiment illustrated in FIG. 7 a-c the bubbles 10 are applied on the wearer facing surface of the topsheet 2 and are before the article is worn (FIG. 7a) covered with a release paper 15, to which the bubbles 10 are attached, for example by an adhesive. When the article is to be used the release paper 15 is removed (FIG. 7b), at which the bubbles 10 will rupture and the probiotic preparation held therein will be released (FIG. 7c).

When using vapour impermeable carrier members the lipid phase becomes less critical Preparation of the Probiotic Preparation and Carrier Member A water suspension of at least one lactic acid producing bacterial strain having a concentration of $10^6$-$10^{15}$ CFU (colony forming units)/ml, preferably $10^{10}$-$10^{13}$ CFU/ml is prepared. The suspension may also contain additional components like contact sorption drying carriers, nutrients and/or protecting agents. Examples of such additional components are given above.

Lactic acid producing bacteria are chosen due to their positive effect in preventing and treating microbial infection in the urogenital area and on the skin. The bacteria are preferably isolated from a healthy person, preferably from the skin or urogenital area of a healthy person. Preferred "lactic acid producing bacteria" include bacteria from the genera *Lactobacillus, Lactococcus* and *Pediococcus*. Preferably the selected bacteria are from the species *Lactococcus lactis, Lactobacillus acidophilus, Lactobacillus curvatus* or *Lactobacillus plantarum*. More preferably the selected bacterium is a *Lactobacillus plantarum* strain. Even more preferably the lactic acid producing bacterium is *Lactobacillus plantarum* 931 (deposition No. (DSMZ): 11918). The lactic acid producing bacteria can be provided alone or in mixtures containing at least two bacterial strains.

The suspension is dried using any of the following techniques: convective drying methods, contact drying methods or by using electromagnetic radiation. Examples of convective drying methods suitable include spray drying, spray granulation and fluidized bed drying. The common feature for convective drying methods is that warm and dry gas flushes around the product and enters into a heat and mass transfer with the product. Convective methods transfer required heat and/or dryness by convection to the wet product. During contact drying, the wet product is stationary in touch with a warm surface or constantly brought into new contact with the warm surface by stirring or revolving. Drying by electromagnetic radiation (infrared or microwave radiation) involves using a belt dryer or a stationary support and submitting the wet product to electromagnetic radiation energy which is being absorbed by the wet product. The absorbed energy serves to warm up the product whereby the moisture in the wet product is evaporated. Drying times using electromagnetic radiation often result in very short drying times.

A probiotic composition is thereafter prepared wherein the dry bacterial composition, comprising lactic acid producing bacteria and optional additional components, is dispersed in a lipid phase which will form the probiotic preparation held in the carrier member. During this step further additional components, such as nutrients for bacterial propagation and skin caring substances can be added to the probiotic composition.

The lipid phase can be composed of a single lipid or a mixture of two or more lipids. The lipid phase due to its hydrophobic character works as a water vapor barrier, thus makes sure that a very low water activity is maintained during storage. In table 2 below a selection of lipids suitable for the core 9 of the capsules 8 is presented.

TABLE 2

| Name | Producer | Melting range | Main ingredients |
| --- | --- | --- | --- |
| Caremelt 107 | Cognis[1] | 25-58° C. | Triglyceride, paraffin, monoglyceride |
| Caremelt 3 | Cognis | 30-47° C. | Triglyceride, paraffin, silicone wax, liquid triglyceride |
| Caremelt 58 | Cognis | 30-49° C. | Triglycerides, polymer wax, stearyl alcohol, silicone wax |
| Vaseline | AC Hud AB[2] | 5-45° C. | Petrolatum |
| Beeswax | Apoteket[3] | | Cera Flava |
| Akosoft 36 | Karlshamn[4] | 34-38° C. | Vegetable fat, hard fat |
| Lipex BC | Karlshamn | 35° C. | Hydrogenated Vegetable oil |
| AMS-C30 | DOW-corning[5] | 70° C. | Silicone wax |

[1]Henkel KgaA, Dusseldorf, Germany
[2]Aco Hud AB, Stockholm, Sweden
[3]Apoteket AB, Produktion och Laboratorier, Gothenburg, Sweden
[4]Karlshamns AB, Karlshamn, Sweden
[5]Seneffe, Belgium The probiotic composition is used in a hygiene absorbent product. For this purpose it is important that the lipid phase has a melting behavior that allows the lipid phase to support bacterial survival and not disturb the absorptive power of the hygiene product.

There is also an upper temperature limit for the melting behavior of the lipid phase. This limit is in part governed by the fact that for mixing the bacterial composition with the lipid phase, the lipid phase has to be soft enough in order to obtain a homogenous mixture. A lipid phase with a too high melting point has to be brought to temperatures that are too high for the bacteria to withstand while being mixed with the lipid phase and therefore a too large portion of the bacteria would die during preparation of the probiotic composition. Also, a lipid phase with too high melting point is not suitable since it does not soften to a high enough extent when in contact with the skin and therefore delivery of the bacteria to the skin is impaired.

The consistency of the core material is influenced by the ratio of bacterial composition to the lipid phase which provide texture and consistency of the core material. By varying the ratio of amount of bacterial composition to amount of lipid phase it is possible to achieve a core material with a suitable consistency.

Therefore, preferably, the lipid phase is in major part solid at room temperature and up to 30° C., becomes softer at body temperature between 30° C. and 40° C., and melting above 60-70° C. However, the lipid phase is still exhibiting soft properties from 30° C. This melting behavior can be achieved by using a single lipid or by mixing different lipids with different melting behaviors in order to achieve the desired melting behavior of the lipid phase.

In order for the lipid phase not to interfere with bacterial survival the water content should be low, below 4% by weight, preferably below 2% and more preferably below 1% by weight. The water vapor transmission rate of the lipid phase, measured according to ASTME 398-83 at 37.8° C. (100° F.) and 90% relative humidity (RH), is 10 $g/m^2/24$ h or less, more preferably 5 $g/m^2/24$ h or less, most preferably 2 $g/m^2/24$ h or less.

The thus prepared probiotic preparation is then applied on a carrier member 10 as disclosed above or encapsulated by a carrier member material to form a bubble or pouch as also described above. The incorporation of the probiotic composition in the carrier member material 10 may be accomplished in different ways, such as conventional polymer processing techniques such as extrusion, film blowing, blow moulding, film casting and vacuum moulding.

The carrier member 10 is applied to an absorbent article in a manner disclosed, either on top of the topsheet 2 or between the topsheet and the absorbent structure 4, so as to allow the probiotic preparation to reach the user of the article.

The invention claimed is:

1. An absorbent article comprising:
   an absorbent structure;
   at least one carrier member located on a wearer facing side of the absorbent structure; and
   a bacterial composition contained in a lipid phase deposited in or on the carrier member to prevent significant transfer of the lipid phase into the absorbent structure before use of the absorbent article, the carrier member, at least before use of the article, being substantially impermeable to the lipid phase,
   wherein the bacterial composition contains at least one lactic acid producing bacterial strain, and said carrier member at least partly encloses the lipid phase containing the bacterial composition.

2. The absorbent article as claimed in claim 1, wherein said carrier member comprises a sheet having at least one pocket or well formed therein containing the lipid phase and bacterial composition.

3. The absorbent article as claimed in claim 2, wherein said pocket or well has a depth of at least 2 mm.

4. The absorbent article as claimed in claim 3, wherein said pocket or well has a depth of no more than 10 mm.

5. The absorbent article as claimed in claim 2, wherein said carrier member is provided with at least two pockets or wells containing the lipid phase and bacterial composition.

6. The absorbent article as claimed in claim 5, wherein said pockets or wells are located spaced apart a distance of at least 5 mm.

7. The absorbent article as claimed in claim 6, wherein said pockets or wells are spaced apart in the longitudinal direction of the article.

8. The absorbent article as claimed in claim 2, wherein said at least one pocket or well is covered by a cover material that at least before use of the article is impermeable to the lipid phase.

9. The absorbent article as claimed in claim 8, wherein the cover material is composed of the same or a different material as the carrier member and is upon use of the article removable by melting, dissolving, peeling off and/or rupturing.

10. The absorbent article as claimed in claim 1, wherein said lipid phase containing the bacterial composition is completely enclosed by the carrier member, which is in the form of a bubble, tube or pouch.

11. The absorbent article as claimed in claim 10, wherein at least part of said bubble, tube or pouch has a minimum cross dimension of at least 2 mm.

12. The absorbent article as claimed in claim 10, wherein the carrier member comprises at least two of said bubbles, tubes or pouches each containing the lipid phase and bacterial composition.

13. The absorbent article as claimed in claim 12, wherein said bubbles, tubes or pouches are located spaced apart a distance of at least 5 mm.

14. The absorbent article as claimed in claim 13, wherein said bubbles, tubes or pouches are spaced apart in the longitudinal direction of the article.

15. The absorbent article as claimed in claim 10, wherein the carrier member upon use of the article is opened to release the lipid phase with the bacterial composition held therein, by melting, dissolving, peeling open and/or rupturing.

16. The absorbent article as claimed in claim 1, wherein the lipid phase is a wax and/or an oil.

17. The absorbent article as claimed in claim 16, wherein the wax is chosen from a plant wax, a mineral wax, an animal wax, a silicon wax and mixtures thereof.

18. The absorbent article as claimed in claim 17, wherein the wax is a mineral wax.

19. The absorbent article as claimed in claim 18, wherein the mineral wax contains petrolatum as a main component.

20. The absorbent article as claimed in claim 1, wherein the carrier member is chosen from polymer films, metal foils and laminates there from.

21. The absorbent article as claimed in claim 20, wherein the polymer film is water soluble.

22. The absorbent article as claimed in claim 20, wherein the carrier member material is chosen from the following materials: polyethylene, polypropylene, polyamide, polyesters, polyurethanes, polyvinyl alcohols, polyvinylacetate, polyethers, ionomers and copolymers thereof, aluminium foil, laminates of polymer films and aluminium foil.

23. The absorbent article as claimed in claim 1, wherein the carrier member material is water vapour impermeable.

24. The absorbent article as claimed in claim 23, wherein the carrier member material is a laminate of aluminium foil and polymer film.

25. The absorbent article as claimed in claim 24, wherein the aluminium foil has a thickness of at least 9 μm.

26. The absorbent article as claimed in claim 1, wherein said at least one carrier member holding the lipid phase and bacterial composition is applied on the wearer facing side of the article or below one or more layers of the article permitting penetration of the lactic acid producing bacterial strain to the wearer.

* * * * *